United States Patent [19]

Vellucci et al.

[11] Patent Number: 5,516,515
[45] Date of Patent: May 14, 1996

[54] SEPARATION OF ALPHA INTERFERON RECEPTOR PROTEINS AND ANTIBODIES THEREFOR

[75] Inventors: Laura C. Vellucci, Union Township; Steven R. Scott, Spotswood; Mei-June Liao, Monmouth Junction; Douglas Testa, Neshanic, all of N.J.

[73] Assignee: Interferon Sciences, Inc., New Brunswick, N.J.

[21] Appl. No.: 519,357

[22] Filed: May 3, 1990

Related U.S. Application Data

[63] Continuation of Ser. No. 826,322, Feb. 5, 1986, abandoned.

[51] Int. Cl.$^6$ .......................... A61K 39/00; C07K 14/715
[52] U.S. Cl. .................................... 424/184.1; 424/198.1; 530/350; 530/351; 530/395; 514/2; 514/8
[58] Field of Search .................................... 530/351, 413, 530/350, 395; 424/184.1, 198.1

[56] References Cited

PUBLICATIONS

C. R. Faltynek, et al. PNAS 80: 3269–73, Jun. 1983, Characteriz. of an interferon receptor . . .
Hannigan, G. E. et al. Eur J. Biochem 157: 187–193. 1986. Differential human interferon . . .
Eid, P. et al. FEBS 156(1):157–160. Jun. 1983. Isolated interferon α–receptor complex . . . Traub, A et al. JBC 259(22): 13872–7. Nov. 1984. Purification and Properties . .

Chemical Abstracts, vol. 99. Abstract No. 36944u, 1983.
Chemical Abstracts, vol. 105, Abstract No. 224075c, 1986.
Chemical Abstracts, vol. 101, Abstract No. 189489j, 1984.
Chemical Abstracts, vol. 101, Abstract No. 189491d, 1984.
Chemical Abstracts, vol. 104, Abstract No. 86869, 1986.
Chemical Abstracts, vol. 100, Abstract No. 21287x, 1981.
Chemical Abstracts, vol. 97, Abstract No. 214016m, 1982.

*Primary Examiner*—Thomas Cunningham
*Attorney, Agent, or Firm*—Howson and Howson

[57] ABSTRACT

Two distinct alpha interferon receptor proteins have been separated and partially purified by antigen affinity chromatography and SDS-PAGE. These proteins are potentially useful as therapeutic agents. Antibodies against these proteins are potentially useful as diagnostic and therapeutic agents.

4 Claims, 5 Drawing Sheets

SEPARATION OF ALPHA INTERFERON RECEPTOR PROTEINS AND ANTIBODIES THEREFOR

This is a continuation, of application Ser. No. 06/826,322, filed Feb. 5, 1986, entitled Separationof Alpha Interferon Receptor Proteins and Antibodies Therefor, now abandoned.

FIELD OF THE INVENTION

The invention relates to the separation and characterization of two alpha interferon receptor proteins, and the preparation of antibodies therefor.

BACKGROUND OF THE INVENTION

Interferons (IFNs) are a group of proteins, some of which are glycosylated, that elicit a variety of cellular responses. These effects include the induction of an antiviral state, inhibition of cell proliferation and modulation of immune responses. The antiviral activity, and possibly the other biological effects of IFN, involve the cellular activation of specific gene products. Friedman, et al., Cell, 38: 745 (1984). The initial step required for the induction of these events within the cells appears to be the binding of IFN to its specific cell surface receptors. This may be followed by the internalization of the IFN-receptor complex and the degradation of the IFN molecules in the lysosome. Branca, et al., J. Biol. Chem. 257: 13291 (1982); Feinstein, et al., J. Interf. Res., 5:65 (1985); Yonehara, et al., J. Gen. Virol., 64: 2409 (1983); Sarkar and Gupta, Eur. J. Biochem., 461 (1984). Alternatively, the interaction of IFN with its specific binding site may stimulate a transmembrane signal which triggers IFN-induced cellular responses.

The ability of interferon to induce antiviral activity has been shown to depend on initial binding of interferon to a specific cell surface receptor. Zoon, Pharmac. Ther., 24: 259–78 (1984); Friedman, Science, 156: 1760–61 (1967); Stewart II, et al., J. Virol., 10:707–712 (1072); Berman and Vilcek, Virology, 57: 378–86 (1974); Branca, et al., J. Biol. Chem., 257:13291–96 (1982); Zoon, et al., Virology, 130:195–203 (1983).

Joshi et al., (1982) covalently bound radiolabeled IFN-alpha-2 to its receptor on Daudi cells, a human lymphoblastoid cell line. They identified, by polyacrylamide gel electrophoresis, a discrete IFN-receptor complex with an apparent molecular weight (mr) of 150,000 daltons.

Faltynek, et al., PNAS, 80: 3269–73 (1983) solubilized the interferon receptor of lymphoblastoid Daudi cells and reported on its binding properties and physical characteristics.

Eid and Mogensen, FEBS Lett., 156:157–160 (1983) extracted and stabilized an allegedly homogeneous, 230,000 dalton complex of interferon bound to interferon receptor. They also detected a second interferon complex, active at 37° C. See also Mogensen, et al. Am. J. Cancer, 28: 575–82 (1981); Mogensen and Bandu, Eur. J. Biochem. 134: 355 (1983). The second complex was believed to represent a transfer of interferon to an activation complex on the cell membrane.

Branca and Baglioni, Nature, 294:768–770 (1981) reported that Daudi cells express a homogeneous population of receptors for IFN alpha-A, but this finding was challenged by Hannigan, et al., J. Biol. Chem., 259, 9456–60 (1984).

Traub, et al., J. Biol. Chem. 258: 13872–77 (Nov. 25, 1984) described the partial purification of alpha interferon receptor activity from human lymphoblastoid cells. The "receptor" was characterized only by stokes radius (74 angstroms) and sedimentation coefficient (13.6S). The stokes radius was between that of thyroglobulin (660,000D) and apoferritin (460,000D). The sedimentation coefficient was between that of galactosidase and catalase. These figures may reflect the formation of micelles of the receptor protein with the Triton detergent employed. There is no suggestion in this paper that there might be more than one receptor present.

The following articles relate to the isolation, purification, and use of other receptor proteins: Hack, et al., Nature, 277:403 (1979) (EGF); Cohen, et al., J. Biol. Chem, 255:4834 (1980) (EGF); Siegel, et al., J. Biol. Chem., 256:9266 (1981) (insulin); Jacobs, et al., 80:1228 (1983) (insulin); Jacobs, et al., Biochem. & Biophys. Res Commun., 77:981 (1977) (insulin); Petruzzelli, et al., DNAS, 81:3327 (1984) (insulin); Greene, et al., PNAS, 77:5115 (1980) (estrogen); Oppenheimer and Czech, J. Biol. Chem., 258:8539 (1983) (rat) IGF II); Cuatrecasas, PNAS, 69:1277 (1972) (insulin).

It has recently been reported that an anti-idiotypic monoclonal antibody was made using rabbit anti-IFN-alpha as the antigen. Osheroff, J. Immunol., 135:306 (1985). This monoclonal antibody (McAb) can recognize human IFN-alpha receptors. Our approach to produce anti-IFN-receptor antibodies employed a different antigen, i.e. the human Type I (alpha and beta) IFN receptor itself.

Our own work was first described by us at the 17th Miami Winter Symposium, Advances in Gene Technology: Molecular Biology of the Immune System, in an Abstract by L. A. Cook, M. J. Liao, S. Scott, and D. Testa, entitled, "Characterization and Affinity Purification of Alpha Interferon Receptor," presented no earlier than Feb. 11, 1985. It was subsequently presented at the TNO-ISIR Meeting on the Interferon System, Oct. 13–18, 1985; and at the 14th Annual Meeting of the ISEM, in Israel. These abstracts relate to prior work which does not qualify as prior art.

At the October, 1985 meeting, French researchers Eid and Mogenson reported the separation of IFN-receptor complexes of 650 and 175 kD, and speculated as to the existence of a 100 kD IFN binding protein. This was subsequent to our work and outside the scope of prior art. Moreover, they did not suggest the existence of the lower molecular weight IFN binding protein which we discovered.

SUMMARY OF THE INVENTION

We have partially purified two distinct Type I interferon receptor proteins from lymphoblastoid cells, with apparent molecular weights of 95–105K and 50–63K respectively.

These two proteins may have different affinities for alpha interferon and particularly alpha-2.

Isolation of the receptor proteins allows for determination of receptor active sites and the synthesis and indentification of small non-IFN molecules which would induce the same activities as IFN. These non-IFN peptides may be cheaper to produce and more easily stabilized. They would circumvent the need for cloning IFN.

Receptor proteins or synthetic receptor-like proteins could be used as therapeutic agents which, upon injection into organ transplant patients, bind to and neutralize excess IFN.

Abnormal production of anti-receptor antibodies in certain diseases has been documented. It is conceivable that anti IFN receptor antibody production is associated with certain diseases. Receptor proteins might be given to treat such diseases.

Isolation and sequencing of the IFN receptor protein might facilitate the cloning of the receptor gene and the investigation of receptor gene expression, receptor protein biosynthesis and receptor-ligand transmission of intracellular responses. Elucidation of such phenomena would result in the better use of IFN as a therapeutic agent. It may also elucidate the etiology of certain disease states and lead to disease control or therapy at the genomic level.

Receptor proteins can be used as immunogens for production of anti-receptor antibodies.

An antibody to the IFN receptor may be used as a diagnostic tool for quantifying the number of IFN receptors on a select cell population such as blood lymphocytes or tumor cells. Correlation of receptor site numbers with certain disease states may be useful for disease diagnosis and the development of clinical assays for the detection of such disease. This information may also reveal a patient's sensitivity to IFN before its use as a therapeutic agent.

Anti-IFN receptor antibodies conjugated to an immunotoxin may be useful as a therapeutic agent which selectively binds to and eliminates virus-infected cells which may express an enhanced number of IFN receptors.

An antibody to the IFN receptor may be useful as a therapeutic agent since it may elicit the same response as IFN itself.

The receptor proteins are isolated as follows:

(1) Daudi cells are pulsed with $^{35}$S-methionine;

(2) The cells are solubilized and passed over an interferon alpha-2-conjugated Sepharose column;

(3) the bound interferon receptor proteins are eluted with 0.1M citric acid buffer at pH 2.0, followed by the return to neutral pH with PBS;

(4) The individual receptor proteins are further purified and identified on SDS-PAGE.

DETAILED DESCRIPTION OF THE INVENTION

MATERIALS AND METHODS

Cell Cultures

Human lymphoblastoid Daudi cells were grown in suspension cultures in RPMI 1640 medium supplemented with 20% heat-inactivated fetal calf serum (FCS), 2 mM L-glutamine, 100 U/ml penicillin and 100 ug/ml streptomycin. Cells were maintained in exponential growth by dilution at 3 day intervals with fresh media until a density of $4 \times 10^5$ cells/ml was obtained. Most experiments were carried out using reinforced minimal essential media (R-MEM) supplemented with 5% FCS (w/v). R-MEM is prepared by supplementing MEM with glucose (3.65 grams/liter) sodium pyruvate (0.11 grams/liter), ferric nitrate (0.167 mg/liter), glutamine (2 mM), amino acids and vitamins.

Interferon

Recombinant human IFN-alpha-2 was synthesized in yeast and purified by immuno affinity chromatography (specific activity $=2 \times 10^8$ U/rag of protein). Ultrapure natural interferon alpha was prepared by incubating human peripheral blood cultures with Sendai virus. The culture supernatant was purified over an anti-interferon alpha column (NK-2 sepharose). The purified natural interferon had a specific activity of $5.7 \times 10^6$ U/mg of protein. Human fibroblast IFN beta was purchased from Lee BioMolecular Research Inc. (San Diego, Calif.), and had a reported specific activity of $4.7 \times 10^5$ U/mg of protein. Human IFN gamma was produced in human peripheral blood cultures containing lymphocytes stimulated with phytohemagglutinin and was purified by affinity chromatography (specific activity $=2 \times 10^7$ U/rag of protein). The biological activity of interferons alpha, beta and gamma were determined by the cytopathic effect (CPE) assay on human HEp-2 cells challenged with vesticular stomatitis virus (Indiana Strain). All titers were calibrated against the NIH reference standards for alpha (#Ga23-902-503) and gamma (Gg 23-901-530) interferons. All titers are expressed as NIH reference units.

Iodination of IFN-alpha-2.

IFN-alpha-2 (0.1 mg) was labeled with $^{125}$I-Bolton-Hunter reagent (1.0 mCi) (Ref.). The iodinated IFN was mixed with human serum albumin (HSA) and purified by gel filtration on a Sephadex G-25 column to remove unattached radiolabel. The iodinated IFN-alpha retained greater that 95% of its original antiviral activity. Fractions were tested for purity by SDS PAGE followed by autoradiography of the gel. Autoradiographic analysis demonstrated the presence of radiolabelled IFN with a Mr of 18,000 daltons and the presence of a minor band (less than 5% of the total) with an Mr of 16,000 daltons. The IFN-containing fraction had 75% of its radioactivity associated with trichloroacetic acid precipitable material and a specific activity of 50 Ci/mmole.

IFN Binding to Various Cell Lines

Cell suspensions ($5 \times 10^7$/ml) containing either human Daudi cells or murine NS-1 cells were incubated with ultrapure IFN (250 units/ml) at 37°. All cultures were rotated during the incubation period and aliquots of the cell suspensions were removed at various time points. The suspensions were centrifuged at 450 x g for 10 mins. and the resulting supernatants were stored at 4° until assayed for IFN activity.

IFN Binding Over Time

Daudi cells (3.5×10⁶) were incubated with $^{125}$I-IFN- 2 (2000U) at 37° C. At various time points, ranging from 5 minutes to 120 minutes, cells were harvested and washed 3 times with cold media. The cell pellet-associated radioactivity was determined using a Gamma 8000 counter (Beckman).

IFN-alpha$_2$ Binding Assays and Competition Experiments.

Daudi cells were resuspended in R-MEM (2.2'106 cells/ml) and 1.33 ml of the cell suspension was aliquoted into each 2 ml well of a 24 well Nalgene plate. Varying amounts of iodionated IFN-alpha-2, alone or in the presence of 100 fold excess of unlabeled IFN-alpha-2, were added to the cell cultures. Binding was carried out for 45 minutes at 37° C. after which the cells were transferred to Eppendorf tubes and washed two times with cold medium. The amount of radioactivity bound to the cells was determined using a Gamma 8000 counter (Beckman). Specific binding activity was determined by subtracting the radioactivity bound to the cells in the presence of a 100 fold excess of unlabelled IFN-alpha-2, from the radioactivity bound in the presence of $^{125}$I-IFN-alpha-2 alone.

Binding at 4° C. was determined similarly, except that the incubation period was 2 hours, and sodium azide was present.

Competition experiments were performed as described above with the exception that Daudi cells (2.5×10⁶) were incubated with a constant amount of 125I-IFN-alpha-2 (700 U) and increasing amounts of unlabeled IFN-alpha-2, natural IFN alpha, natural IFN beta or natural IFN gamma.

Cross Linking of $^{125}$I-IFN-alpha-2 to Whole Cells and Plasma Membranes.

a. Whole Cells:

Daudi cells were washed one time in RPM1 1640 medium and resuspended in 40 ml of the same medium supplemented with 2% FCS (1×10⁷ cells/ml).

The cell suspension was divided equally between two 75cm² tissue culture flasks. Flask A received $^{125}$I-IFN-alpha-2 (3000 U/ml). Flask B received the same amount of labeled IFN and, in addition, a 30 fold excess of unlabeled IFN-alpha-2 (1×10⁵ U/ml). Following a 45 minute incubation period at 37°, the cells were washed two times and resuspended in phosphate buffered saline containing Ca$^{++}$ and Mg$^{++}$ ions (1 mM). They were chilled to 4° and treated with a noncleavable, crosslinking agent, disuccinimidyl suberate (DSS) (0.3 mM) for 20 minutes. Excess DSS was removed by washing the cells in PBS containing phenylmethylsulfonyl fluoride (PMSF) (2mM). The cells were frozen at −80°, thawed and lysed in a buffer A (0.02M boric acid, 0.2 mM EDTA, pH 10.2). The material was clarified by centrifugation at 500 xg for 8 minutes. The resulting supernatant was centrifuged at 26,500 xg for 45 minutes and the membrane rich pellet was dissolved in SDS containing Laemmli sample buffer. The samples were electrophoresed on a 7.5% SDS-polyacrylamide gel.

b. Plasma Membranes:

Daudi cells (8×10⁹) were lysed in 80 ml of buffer A (pH 10.2) for 15 minutes with constant stirring as described by Thom (1977). The material was filtered through 2 layers of nylon gauze and stored at 4° C. overnight. Phenylmethylsulfonyl fluoride (PMSF) (2 mM) was added on the following day and the material was clarified by centrifugation 400 xg for 7 minutes. The resulting supernatant was concentrated 8 fold in an Amicon stirred cell apparatus containing a YM 10 membrane filter and dialyzed three fold against PBS. The crude membrane concentrate, which had a final volume of 10 ml, was adjusted to pH 8.0 with 1 M HCl. A one ml aliquot was incubated with $^{125}$I-IFN-alpha-2 (7'10³ units) for 80 min. at 37° C. with continuous shaking. The sample was incubated with DSS (0.1 mM) at 4° for 20 min. and centrifuges at 150,000 x g for 2 hours. The pellet was resuspended in 40 µl of SDS containing sample buffer and applied to a 7.5% polyacrylamide gel.

c. Gel Electrophoresis:

Gel electrophoresis was carried out in slab gels containing 7.5% polyacrylamide. In some instances, gels were soaked in Enlightening (New England Nuclear) prior to drying. Autoradiography studies were performed by exposing a gel to Kodak-X-omat film in the presence of a DuPont Cronex Lightening plus intensifying screen.

Affinity Purification of Radiolabeled Receptor Proteins a. IFN Affinity Column Preparation:

Activated CH-Sepharose 4B (0.35g) which couples ligands at the ends of 6-carbon spacer arms, was used as an immunopurification support. It was washed with 70 ml of 1 mM HCl (pH 2.9) for 15 minutes. The gel was rinsed once with buffer B (0.1M NaHCO$_3$, 0.5M NaCl pH 8.0 ) and mixed with 1.8 mg of IFN-alpha-2 in 6.5 ml of the same buffer. The mixture was rotated for 1H at room temperature, washed once with buffer B, and the remaining active groups were blocked by incubation with Tris HCl (0.1M, pH 8.0 ) for 60 minutes. The IFN-sepharose preparation was washed with three cycles of Buffer B, Buffer C (0.05M tris, 0.5M NaCl, pH 8.0) and buffer D (0.05M acetic acid; 0.5M NaCl, pH 4), and the resin was packed into a disposable column. The gel (total volume =1.0 ml) was pretreated with buffer E (0.15M phosphate buffered saline with 10 mM Chaps and 1 mM PMSF, 0.025% NAN$_3$, pH 7.2) and buffer F (0.1M citric acid, 10 mM Chaps, 0.5M NaCl, pH 2.0) before use.

b. Biosynthetic $^{35}$S-methionine Labelling of Daudi Cells:

Daudi cells (4×10⁹) were washed twice in prewarmed (37° C.) methionine-free RPMI 1640 medium and resuspended in 75 ml of prewarmed methionine-free RPMI 1640 medium supplemented with 2 mM L-glutamine, antibiotics, 10% FCS and 2 mCi of $^{35}$S-methionine (Amersham, specific activity =1435 Ci/mmole). The cells were incubated for 16 hours at 37° in a 150 cm² T flask.

c. Cell Solubilization and Affinity Purification:

Radiolabeled cells were washed twice with cold RPMI 1640 medium containing 0.02% NaN$_3$ and solubilized in 30 ml of buffer E supplemented with 10 ug/ml of micrococcal nuclease. The mixture was rotated for 80 minutes at 37° C. and filtered through 2 layers of nylon gauze. The material was clarified by a low speed centrifugation at 450 x g for 8 min, followed by high speed centrifugation at 100,000 xg for 80 min. The resulting supernatant (37 ml) was passed through a 0.45 µm Nalgene filter, treated with 1 mM PMSF and loaded, at a flow rate of 0.3 ml per minute, onto an IFN affinity column. The column was washed extensively with buffer E (pH 7.2) prior to its elution with buffer F at pH 2.0. It was then returned back to neutral pH with buffer E. Select elution fractions were pooled, dialyzed against 10mM phosphate buffer containing.1% SDS and concentrated 10 fold using a CX-10 immersible concentrator (Millipore). Samples were mixed with glycerol and B-mercaptoethanol prior to electrophoresis on a 7.5% polyacrylamide gel The gel was soaked in Enlightening (New England Nuclear) prior to drying and autoradiography.

EXAMPLE 1: BINDING STUDIES

Adsorption of IFN by human and mouse cell lines was assessed by comparing the total amount of IFN added to each cell culture and the amount of IFN which remained in the culture supernatant following a 20 minute incubation period at 37°. The IFN activity in the human Daudi cell culture supernatant at t=20 minutes was reduced by 75% as compared to control values in which IFN was incubated with media alone. In contrast, IFN activity was not absorbed from the culture supernatant of murine NS-1 cells. These data indicate that the human cells tested, but not the mouse cells tested, express cell surface receptors for human leukocyte IFN. The remaining studies were carried out using $^{125}$I-IFN-alpha-2 and Daudi (human lymphoblastoid) cells. Cell-associated radioactivity increases dramatically within the first 30 minutes but levels off after 45 minutes of incubation, suggesting receptor saturation with $^{125}$I-IFN-alpha-2. The specific binding of $^{125}$I-IFN-alpha-2 to Daudi cells was determined by subtracting the non-specific counts from the total counts bound at 37° and at 4°. The specific binding of $^{125}$I-IFN, at both temperatures, increases with the addition of increasing amounts of IFN. Cells incubated at the higher temperature for 45 min. bind more IFN than those incubated at the lower temperature for 2h. A plateau in the specific binding curve is apparent only on those studies performed at 37°.

Figure 2:
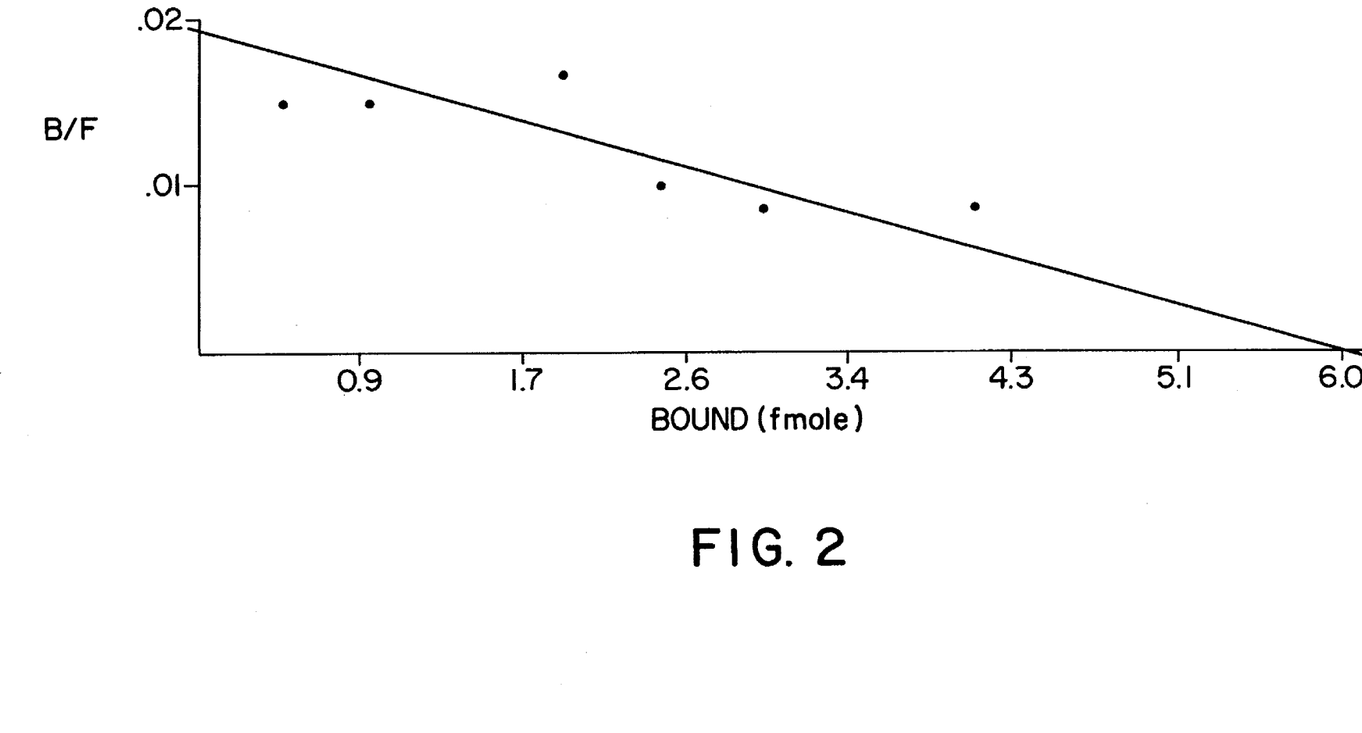
FIG. 2 is a Scatchard plot analysis of the binding of radiolabelled interferon alpha-2 to Daudi cells following incubation for 2 hours at 4° C.

Scatchard plot analysis of the binding data at 4° (FIG. 2) results in a straight line, suggesting the expression of a single binding affinity. The dissociation constant of the interaction was calculated to be $1.5 \times 10^{-10}$M and there are about 800 such receptor sites per cell.

Scatchard plot analysis (FIG. 1) of the binding data obtained at 37° results in a curvilinear plot, indicating the presence of receptor sites with at least 2 binding affinities. The slopes of the tangents of the curved plot yield 2 apparent dissociation constants (Kd). The high affinity and low affinity binding sites have Kd's of about $8 \times 10^{-11}$ M and $1 \times 10^{-9}$ M, respectively. The intercepts on the X axis (abscissa) of these tangents indicate the Daudi cells express approximately 1300 high affinity and 4500 low affinity sites per cell.

Figure 1:
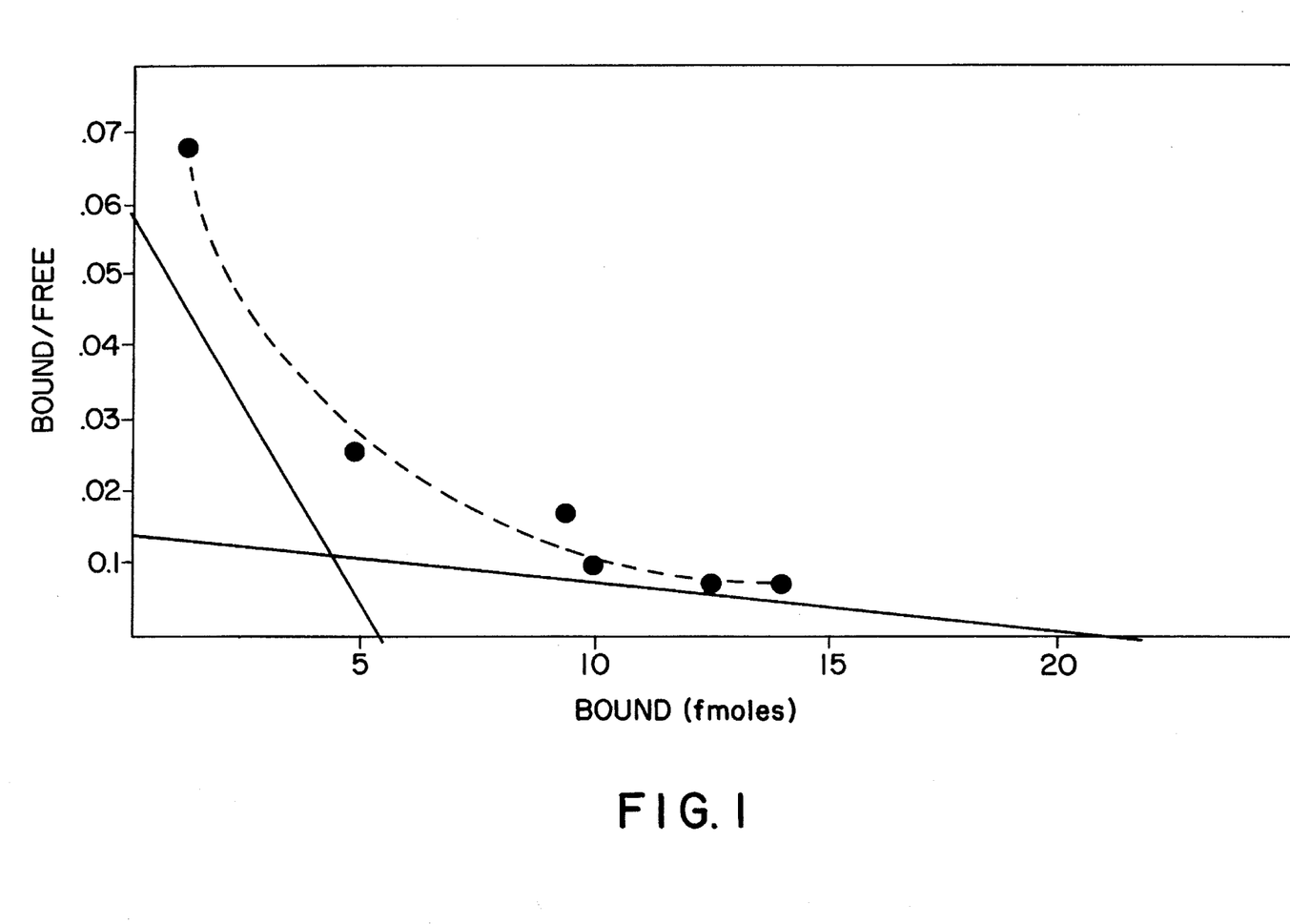
FIG. 1 is a Scatchard plot analysis of the binding of radiolabeled interferon alpha-2 to Daudi cells following incubation for 45 mins at 37° C. It suggests the expression of two or more types of binding sites.

Detection of both the high and low affinity receptor sites appear to require more favorable binding conditions, as provided at the higher temperature.

Competition experiments (FIG. 3) show that a 100 fold excess of unlabeled IFN-alpha2, natural (N) IFN alpha or IFN beta results in a more than 80% reduction in the binding of $^{125}$I-IFN-alpha2 for Daudi cells. IFN-gamma does not compete for binding to this site.

Figure 3:
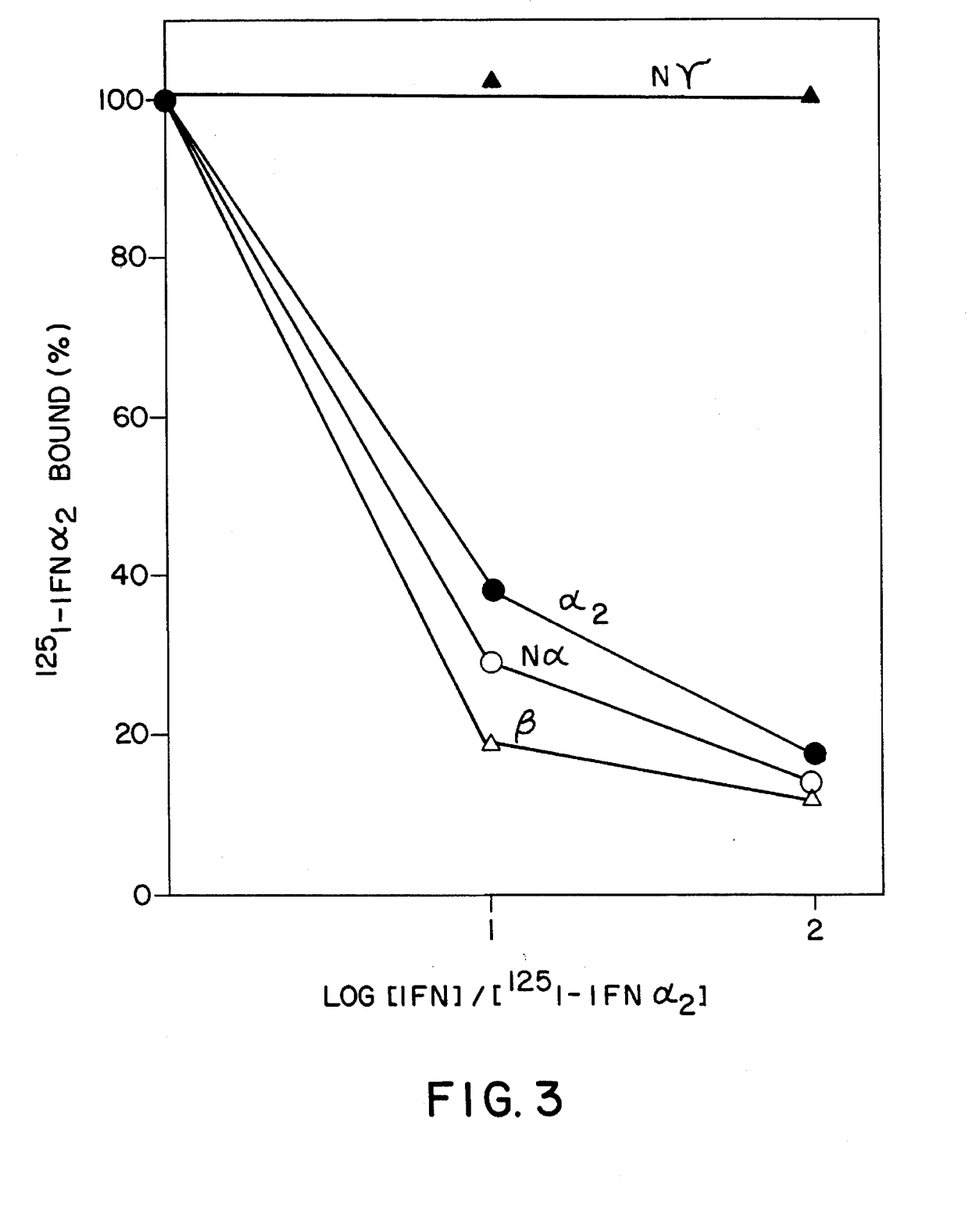
FIG. 3 is a competitive binding assay which measures the ability of unlabeled interferon alpha-2, natural interferon alpha (a mixture of alpha subtypes), interferon beta and interferon gamma to displace radiolabeled interferon alpha-2 from Daudi cell receptor sites.

These results indicate that alpha and beta interferons bind to the same or closely related receptor sites on Daudi cells, and that gamma interferon does not normally bind to the same receptor (or receptors) as alpha and beta.

EXAMPLE 2: IDENTIFICATION OF THE IFN RECEPTOR PROTEIN

Figure 4:
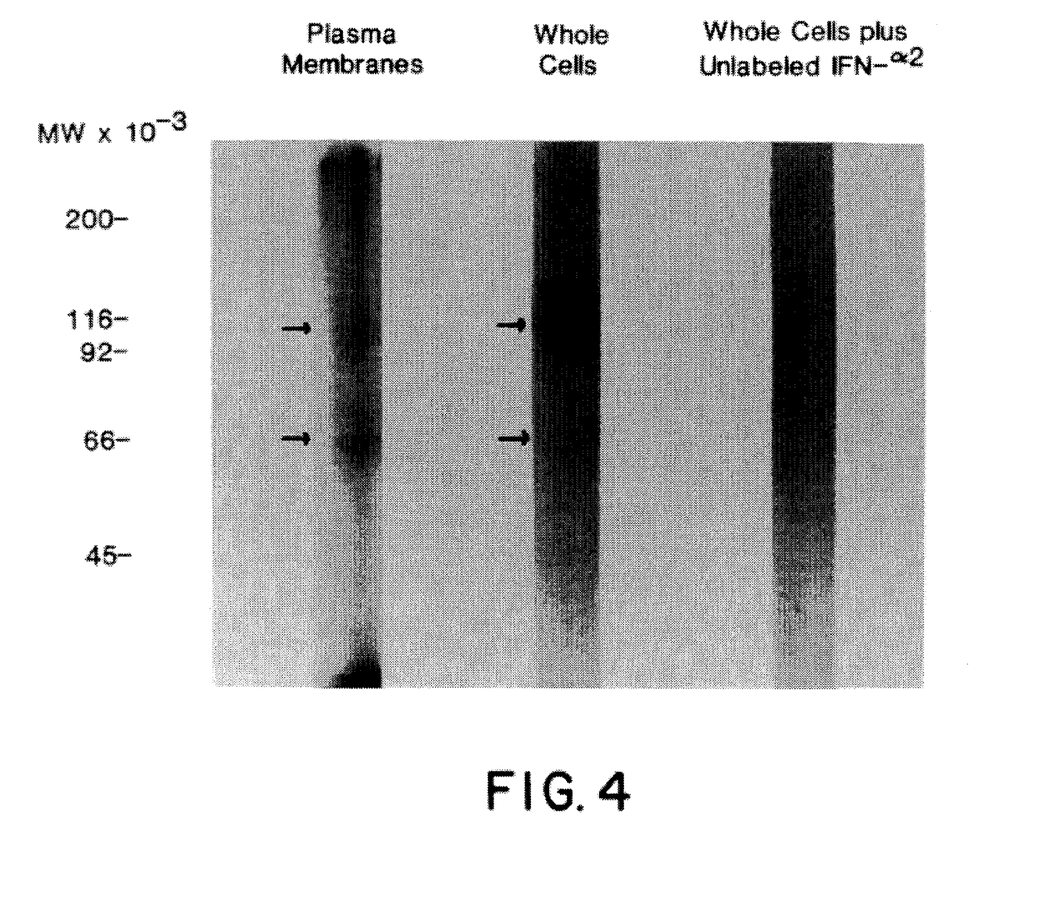
FIG. 4 is an autoradiograph of radiolabeled alpha interferon cross-linked to whole cells and plasma membranes.

IFN-alpha was covalently linked to its receptor protein on Daudi cells by the addition of the noncleavable crosslinking reagent, DSS. The IFN-receptor complex was solubilized and electrophoresed on a polyacrylamide gel. Autoradiography reveals the presence of a dark band with a Mr of 112,000 daltons and a lighter band with a Mr of 66,000 daltons (FIG. 4). These bands are apparently representative of two $^{125}$I-IFN-receptor complexes. Substracting the Mr of IFN (18,000 daltons) from that of the complexes, and rounding off, results in the determination of 2 receptor proteins with Mr's of approximately 95,000 daltons and 50,000 daltons. Experiments performed in which cells were incubated with $^{125}$I-IFN-alpha2 and excess unlabeled IFN-alpha2 did not result in the detection of these bands. These findings suggest that Daudi cells express two cell surface proteins which specifically bind IFN-alpha2. Crosslinking of $^{125}$I-IFN-alpha2 to crude Daudi cell plasma membrane preparations also resulted in the detection of the 112,000 dalton and 66,000 dalton bands. (FIG. 4) In these experiments, the high and the lower molecular weight bands were found at similar intensities.

EXAMPLE 3: AFFINITY PURIFICATION OF IFN-ALPHA-2 RECEPTORS

IFN receptor proteins were isolated from Daudi cells by affinity chromatography. Daudi cells were cultured with $^{35}$S-methionine in order to radiolabel all newly synthesized proteins. Cells were solubilized in a non-denaturing detergent, Chaps, and radiolabeled receptor proteins were affinity purified by passage over an IFN-alpha2 column. The affinity column was prepared by covalently linking IFN to sepharose via an active ester group at the end of a 6 carbon spacer arm. This system was chosen in order to minimize steric hindrance during the binding of receptor proteins to IFN-alpha2.

Figure 5:
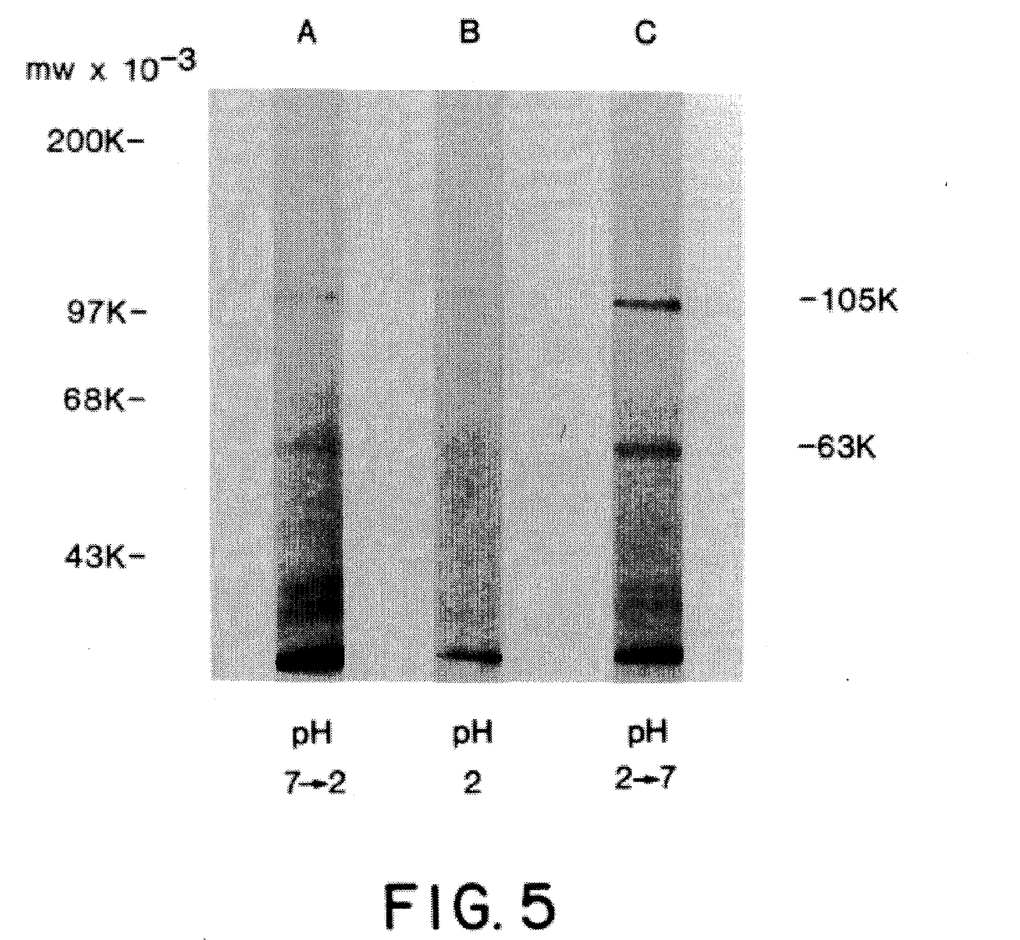
FIG. 5 is a fluorograph of the Daudi cell proteins which had been bound to an interferon alpha-2 conjugated Sepharose column and which were eluted with a citric acid buffer at various pH values.

Daudi cells cultured overnight in met-free medium supplemented with 2 mCi of $^{35}$S-methionine ($5 \times 10^9$ cpm) remained more than 70% viable and at the same initial cell concentration ($5 \times 10^7$/ml). The cells were harvested and solubilized in buffer E as described above. 27% ($1.37 \times 10^9$ cpm) of the total radioactivity added remained associated with the solubilized material (40 ml) and was loaded on to the IFN-alpha2 Sepharose column. 98% of the radioactivity applied to the column was recovered in the flowthrough. Elution fractions were analyzed by SDS-PAGE and fluorography (FIG. 5).

The gel fluorograph shows that fraction A contains 2 predominant bands with Mr's of 105,000 daltons and 63,000 daltons. A doublet with a Mr of less than 45,000 daltons is also visible as well as other faint bands. Fraction A was collected during the conversion of the column from pH 7.0 to pH 2.0. Fraction B was collected when the column pH was equal to 2.0. It contains the same bands as in fraction A but with less intensity. Fraction C was collected during the reversion of the column from pH 2.0 back to pH 7.0. It also contains the predominant 105,000 dalton and 63,000 dalton bands. These data would suggest that there are two proteins which have a strong affinity for IFN-alpha2 and are therefore likely candidates to be the IFN receptor proteins.

EXAMPLE 4: PREPARATION OF ANTIBODIES TO HUMAN INTERFERON-ALPHA RECEPTOR PROTEINS

Balb/C mice were immunized with one of three different immunogen preparations: (1) intact interferon-sensitive cells; (2) partially purified Daudi cell membranes; or (3) receptor proteins purified according to example 3, but without radiolabelling.

The injection protocols for all three imunogen preparations were as follows, respectively: (1) intact interferon sensitive cells, 6 injections (0.5–1.0×10⁷ cells per inj.) given intraperitoneally without adjuvant over a 3 month period; (2) partially purified Daudi plasma membranes, 11 injections (10 ugs per inj.) given intraperitoneally with and without adjuvant over a 14 month period; or (3) receptor proteins purified according to example 3 without 35 S-labeling, 12 injections (3.2 ugs per inj.) given intraperitoneally with and without adjuvant over a 12 month period.

Relative antibody production was monitored using a competitive binding assay in which the antibodies compete with $^{125}$I-IFN-alpha2 for the Daudi cell surface receptors. The results demonstrate a positive response only in mice immunized with the affinity purified alpha-interferon receptor proteins. This response was evident by the 3rd injection and within 3 to 4 weeks after the first injection. The maximum response was observed by week 4 and remained high through week 31. The antiserum at the dilution of 1:1000, reduced binding of the radiolabelled IFN-alpha to Daudi cells by 80% or more. This antiserum did not contain antibody to IFN-alpha since it could not detect IFN in an immunoblot assay. The spleen cells of the immunized mouse were separated into equal aliquots. One half of the cells were fused with the mouse myeloma cell line, NS-1-503. The other one half of the spleen cells were injected into a irradiated recipient mouse via intravenous route. The mouse was challenged with antigen and 4 days later the spleen cells were fused with the mouse myeloma cell line, NS-1-503.

The resulting hybridomas may be expected to express antibodies against the interferon alpha receptor proteins.

These antibodies may be used to further purify the receptor proteins by immunopurification.

The above examples are merely illustrative, and are not meant to limit the invention.

LIST OF ABBREVIATIONS

Buffer A=(0.02M boric acid 0.2mM EDTA, pH 10.2)
Buffer B=0.1M NaHCO$_3$, 0.5M NaCl, pH 8.0
Buffer C=0.05M Tris, 0.5M NaCl, pH 8.0
Buffer D=0.05 M acetic acid, 0.5M NaCl, pH 4.0
Buffer E=10mMNaPi, 0.15M NaCl, 10mM Chaps, pH 7.2
Buffer F=0.1M citric acid, 0.5M NaCl, 0.10 mM Chaps, pH 2.3
DSS=Disuccinimidyl suberate
IFN=Interferon
met=Methionine
Mr=Molecular weight
PMSF=Phenylemethylsulfonyl fluoride
PAGE=Polyacrylamide gel electrophoresis
SDS=Sodium Dodecyl Sulfate

We claim: This is a continuation, of application Ser. No. 06/826,322, filed Feb. 5, 1986, entitled SEPARATION OF ALPHA INTERFERON RECEPTOR PROTEINS AND ANTIBODIES THEREFOR, now abandoned.

1. A partially pure protein specifically binding alpha and beta interferon, but not gamma interferon, and having an apparent molecular weight of about 63,000 daltons as determined by affinity chromatography, SDS-PAGE and fluorography, and about 50,000 as determined by crosslinking, SDS-PAGE, and autoradiography, separated from other interferon receptor protein.

2. A partially pure complex of interferon alpha and an interferon-alpha receptor protein, according to claim 1, with a total apparent molecular weight of about 66,000 daltons.

3. An interferon alpha receptor protein according to claim 1 having the identifying characteristics of a Daudi cell interferon-alpha receptor and a dissociation constant for alpha-2 interferon of about $8\times10^{-11}$ M.

4. A pharmaceutical composition comprising a protein according to claim 2, in a pharmaceutically acceptable carrier.

* * * * *

UNITED STATES PATENT AND TRADEMARK OFFICE
CERTIFICATE OF CORRECTION

PATENT NO. : 5,516,515
DATED : May 14, 1996
INVENTOR(S) : Laura C. Vellucci, Steven R. Scott, Mei-June Liao, and Douglas Testa It is certified that error appears in the above-indentified patent and that said Letters Patent is hereby corrected as shown below:

Col. 4, line 24, delete "U/rag" and insert thereof -- U/mg --.

Col. 4, line 36, delete "U/rag" and insert thereof -- U/mg --.

Col. 5, line 17, delete "2.2'106" and insert thereof -- $2.2 \times 10^6$ --.

Col. 6, line 12, delete "7'10$^3$" and insert thereof -- $7 \times 10^3$ --.

Signed and Sealed this

Twenty-seventh Day of August, 1996

Attest:

BRUCE LEHMAN

*Attesting Officer*    *Commissioner of Patents and Trademarks*